(12) United States Patent
Baumeister

(10) Patent No.: US 10,632,234 B2
(45) Date of Patent: Apr. 28, 2020

(54) VACUUM CONTAINER

(71) Applicant: PFM MEDICAL AG, Cologne (DE)

(72) Inventor: Christian Baumeister, Trier (DE)

(73) Assignee: PFM MEDICAL AG, Cologne (DE)

( * ) Notice: Subject to any disclaimer, the term of this patent is extended or adjusted under 35 U.S.C. 154(b) by 196 days.

(21) Appl. No.: 15/406,054

(22) Filed: Jan. 13, 2017

(65) Prior Publication Data

US 2017/0203017 A1 Jul. 20, 2017

(30) Foreign Application Priority Data

Jan. 14, 2016 (DE) .................... 20 2016 100 155 U

(51) Int. Cl.
*A61M 1/00* (2006.01)
*A61M 39/10* (2006.01)
*A61M 39/28* (2006.01)
*A61M 27/00* (2006.01)
*A61M 39/24* (2006.01)

(52) U.S. Cl.
CPC ........ *A61M 1/0025* (2014.02); *A61M 1/0001* (2013.01); *A61M 1/008* (2013.01); *A61M 1/0021* (2013.01); *A61M 27/00* (2013.01); *A61M 39/10* (2013.01); *A61M 39/24* (2013.01); *A61M 39/28* (2013.01); *A61M 2205/0216* (2013.01); *A61M 2205/3379* (2013.01); *A61M 2207/00* (2013.01); *A61M 2209/082* (2013.01)

(58) Field of Classification Search
CPC .............. A61M 1/0001; A61M 1/0003; A61M 1/0015; A61M 1/0021; A61M 1/0025; A61M 1/008; A61M 1/0088; A61M 39/10; A61M 39/28
See application file for complete search history.

(56) References Cited

U.S. PATENT DOCUMENTS

| 4,376,439 A | 3/1983 | Lauterjung |
| 4,522,623 A * | 6/1985 | Lauterjung .......... A61M 1/0011 |
| | | 137/205 |
| 5,238,217 A | 8/1993 | Fell |
| 6,024,731 A | 2/2000 | Seddon et al. |
| 2004/0116902 A1 | 6/2004 | Grossman et al. |

(Continued)

FOREIGN PATENT DOCUMENTS

| DE | 2446470 | 4/1796 |
| DE | 1514659 | 1/1966 |
| DE | 2857311 | 1/1980 |

(Continued)

*Primary Examiner* — Kai H Weng
(74) *Attorney, Agent, or Firm* — Grossman, Tucker, Perreault & Pfleger, PLLC

(57) ABSTRACT

The invention relates to a vacuum container for drainage of fluids or wound secretion, wherein the vacuum container is pre-evacuated, with an inlet opening for connection to a drainage line, wherein at the inlet opening a vacuum indicator is located and that the inlet opening is sealable. The invention further relates to a drainage line for drainage of fluids or wound secretion, wherein the drainage line has a vacuum indicator, wherein the vacuum indicator is designed to indicate a vacuum inside a connected vacuum container. Further the invention relates to a system for drainage of fluids or wound secretion, comprising a vacuum container according to the invention and a drainage line.

18 Claims, 3 Drawing Sheets

(56) References Cited

U.S. PATENT DOCUMENTS

2010/0063464 A1    3/2010  Meyer et al.
2010/0204649 A1*   8/2010  Miller .................. A61M 5/145
                                                        604/134

FOREIGN PATENT DOCUMENTS

DE         8604614       4/1986
DE      102005015878    10/2006

* cited by examiner

VACUUM CONTAINER

FIELD OF THE INVENTION

The invention relates to a vacuum container for drainage of fluids or wound secretion, wherein the vacuum container is pre-evacuated, with an inlet opening for connection to a drainage line.

BACKGROUND

Furthermore, the invention relates to a drainage line for drainage of fluids or wound secretion.

Further, the invention relates to a system for drainage of fluids or wound secretion.

From the prior art vacuum containers are known, like for example Redon-bottles or the like. These Redon-bottles are usually pre-evacuated; hence already during the manufacturing a vacuum is created in the interior of the Redon-bottle. In such a way fluids or wound secretion can be aspirated by the vacuum wound drainage using the suction effect caused by the vacuum. To get a feedback for the user regarding the vacuum in the Redon-bottle, it is known to provide these vacuum containers with vacuum indicators. In particular these are vacuum indicators in the form of a bellow that is located at the Redon-bottle. Due to the distance between the folds of the vacuum indicator relative to each other it is evident whether a vacuum is present in the Redon-bottle or not. Such bellow vacuum indicators usually consist of a flexible material, like for example an elastomer or a thermoplastic elastomer. Disadvantageous is that the materials used for the vacuum indicators are subject to permeation processes, which cause air to enter through the material of the vacuum indicator or through the connections between the vacuum indicator and the Redon-bottle into the interior of the Redon-bottle. This entering air neutralizes the vacuum created during the manufacturing of the Redon-bottle, so that such Redon-bottles cannot be held in stock for a long period.

The lower the capacity of the pre-evacuated Redon-bottle, the more important is the lowest possible permeation of air into the pre-evacuated Redon-bottle for maintaining the vacuum over the storage period of the pre-evacuated Redon-bottle. Because for a small capacity, like e.g. 200 ml, the same amount of air diffused by permeation has a greater influence to the pressure and thus the vacuum inside the Redon-bottle as is the case with a Redon-bottle with a greater capacity, like e.g. 400 ml or 600 ml. This has been evaluated and confirmed by the applicant by exemplary measurements of the remaining vacuum for different storage periods.

Based on this prior art it is an object of the invention to provide a vacuum container or a system for drainage of fluids or wound secretion, which reduces the permeation of air into the vacuum container or into the system.

SUMMARY

For technically solving this object according to the invention a vacuum container for drainage of fluids or wound secretion is proposed, wherein the vacuum container is pre-evacuated, with an inlet opening for connection to a drainage line, which is characterized in that at the inlet opening a vacuum indicator is located and the inlet opening is sealable.

The invention is based on the findings that the durability of the vacuum in pre-evacuated vacuum containers, like for example Redon- or ASEPT-bottles, is particularly limited by the bellow as vacuum indicator located at the vacuum container. In particular air enters into the interior of the pre-evacuated vacuum container by permeation through the material of the vacuum indicator. To increase the durability of the vacuum of the pre-evacuated container it is according to the invention stipulated to provide a vacuum indicator at the inlet opening and that the inlet opening of the vacuum container is designed sealable. If the inlet opening of the vacuum container is sealed, the vacuum indicator of the vacuum container has no function and therefore no air enters by permeation through the vacuum indicator or the connection between vacuum indicator and the vacuum container into the pre-evacuated vacuum container and does not negatively affect the durability of the vacuum. However, if during the usage of the vacuum container for drainage of fluids or wound secretion the inlet opening is opened, the vacuum indicator functions as usual. The inventive solution allows a major reduction or elimination of permeation of air through the material of the vacuum indicator or the connection between the vacuum indicator and the vacuum container to a negligible amount.

The drainage line is preferably tube-like. In the following the features drainage line and drainage tube are used interchangeably.

In a preferred embodiment of the invention the vacuum indicator is connected to the drainage line using a T-shaped connector, so that aspirated wound secretion or aspirated fluids flow past the vacuum indicator. Thereby one free end of the T-shaped connector can be connected to an end of the drainage line and the second free end of the T-shaped connector can be connected to the inlet opening of the vacuum container, so that the vacuum indicator is located at the inlet opening of the vacuum container via the T-shaped connector.

In a preferred embodiment of the invention it is provided that the vacuum indicator has a further inlet opening, to which a drainage line can be connected, so that the drainage of fluids or wound secretion is affected over the vacuum indicator into the vacuum container. Fluids or wound secretion to be aspirated from a body or tissue opening of a human or animal body are thus guided through the vacuum indicator into the vacuum container. Therefore, the vacuum indicator preferably has a channel or the like or builds a channel or the like, so that the fluid or wound secretion to be aspirated is transferable through the vacuum indicator into the vacuum container.

In a preferred embodiment of the invention the vacuum indicator is connected with the inlet opening of the vacuum container via a tube-like element. The tube-like element is located between the inlet opening of the vacuum container and the vacuum indicator. The vacuum indicator is thus located at the inlet opening of the vacuum container using the tube-like element.

Preferably the inlet opening of the vacuum container is sealable by a clampable tube-like element. Since the tube-like element in an embodiment of the invention is connected with one end directly at the inlet opening of the vacuum container and at the other end of the tube-like element the vacuum indicator is located, the inlet opening of the vacuum container can thus be sealed by clamping the tube-like element. For opening the inlet opening of the vacuum container the tube-like element is released, so that it is no longer clamped. If the inlet opening of the vacuum container is sealed, neither fluid or wound secretion can be guided into the vacuum container nor can fluid or wound secretion already located inside the vacuum container exit the vacuum container. This is particularly relevant when changing or ending the drainage, so that the vacuum container can be disposed without accidentally leakage of fluid or wound secretion from the vacuum container caused by the user. Due to the closed inlet opening of the vacuum container the fluid or wound secretion contained in the vacuum container can be afterwards used for further examinations.

In a preferred embodiment of the invention the tube-like element is clampable using a clamping device, preferably by a so-called slide-clamp. A slide-clamp has a recess tapered in a longitudinal direction, wherein the recess is tapered at one end of the slide-clamp is such a way that a tube or tube-like element or the like located inside the recess is pinched off. The opposing end of the recess is in contrast wide enough that a tube or tube-like element or the like located in the recess is not clamped or pinched off.

A further embodiment of the invention provides that the vacuum container has a capacity of about 100 ml to 1500 ml, preferably about 1000 ml. Furthermore, two or more vacuum containers can be connected to each other using a tube-like connecting piece, so that the a capacity of about 2000 ml to about 3000 ml can be achieved by connecting two vacuum containers of each about 1000 ml respectively about 1500 ml.

One embodiment of the invention is characterized in that the vacuum container is pre-evacuated with about 40000 Pascal to about 98000 Pascal. A pre-evacuation of the vacuum container with 98000 Pascal [Pa] corresponds to a so-called high-vacuum drainage, wherein a stronger suction is created from the vacuum container for drainage of fluids or wound secretion, and a pre-evacuation of the vacuum container with about 40000 Pascal [Pa] corresponds to a so-called low-vacuum drainage.

In a preferred embodiment of the invention the vacuum indicator is a bellow, wherein the bellow is contracted for an evacuated container (with a vacuum present) and an opened inlet opening of the vacuum container and an elongated bellow for a non-evacuated vacuum container or for a closed inlet opening of the vacuum container. Due to the bellow it is thus apparent whether a vacuum is present in the vacuum container, so that suction for draining fluids or wound secretion during a drainage at a body and/or tissue opening of the human or animal body is achievable. If no vacuum is present in the vacuum container the vacuum indicator in form of a bellow is elongated, which means that the bellow is relaxed. This is recognizable by the great distance between the folds of the bellow. If a vacuum is present in the vacuum container the distance between the folds of the bellow is smaller, wherein for a completely evacuated vacuum container the distance between the folds of the bellow is minimal. In addition the vacuum indicator can comprise a scale, so that a certain value referring to the amount of vacuum in the vacuum container is indicated to the user.

The vacuum container can further comprise a mounting for hanging and/or fixing the vacuum container preferably to a stand, infusion stand or the like. Furthermore, the pre-evacuatable vacuum container can be provided with a scale for indicating the amount of fluid or wound secretion already located or received inside the vacuum container. This scale provides information about the filling level of the vacuum container.

Due to the inventive solution it is possible to abstain from a maybe more complex vacuum indicator, particularly from a bellow with thicker walls and/or a reduced surface and/or a permeation-reduction coating. Particularly the manufacturing of a bellow with e permeation-reduction coating is very expensive, since this requires an expensive batch-process. These actions serve to reduce the permeation of air into the interior of the pre-evacuated vacuum container and particularly result in higher manufacturing costs. Due to the inventive solution these actions are no longer necessary. For example due to the usage of the inventive solution the vacuum indicator can be manufactured by a cheap injection molding process. Therefore, for example a so-called LSR-injection molding process is suitable, which allows a particularly cheap manufacturing of the inventive solution. The manufacturing can use an injection molding process instead of an extrusion blow molding process, wherein injection molding has shorter cycles, so that more units per time can be manufactured. Since the permeation of air into the pre-evacuated container is reduced according to the invention, the higher permeation due to the used cheap SIK elastomer has no negative impact. Particularly considering that the use-time is very short compared to the storage period and thus most air permeates through the material of the vacuum indicator into the vacuum container over the storage period.

The object of the invention is further solved by a drainage line for drainage of fluids or wound secretion, which is characterized in that the drainage line comprises a vacuum indicator.

In a particularly preferred embodiment of the invention the vacuum indicator is integrated into the drainage line. Advantageously the vacuum indicator is integrated into the drainage line proximate to the end of the drainage line or drainage tube, wherein the drainage line or drainage tube is connected to the inlet opening of the vacuum container with the end comprising the vacuum indicator. The vacuum indicator is thus part of the tube line usage for drainage, which is particularly connected with a drainage catheter for drainage of fluids or wound secretion. The drainage catheter is in turn located in a body and/or tissue opening of the human or animal body.

An embodiment of the invention provides that the drainage line is designed for connection with an inventive vacuum container.

The object of the invention is further solved by a system for drainage of fluids, which comprises a vacuum container according to the embodiments of the invention and a drainage line.

A further embodiment of the invention is characterized in that the drainage line of the system is a drainage line according to the invention.

Further details, features and advantages of the invention will be explained in the following with respect to the embodiments shown in the figures.

DETAILED DESCRIPTION

Figure 1:
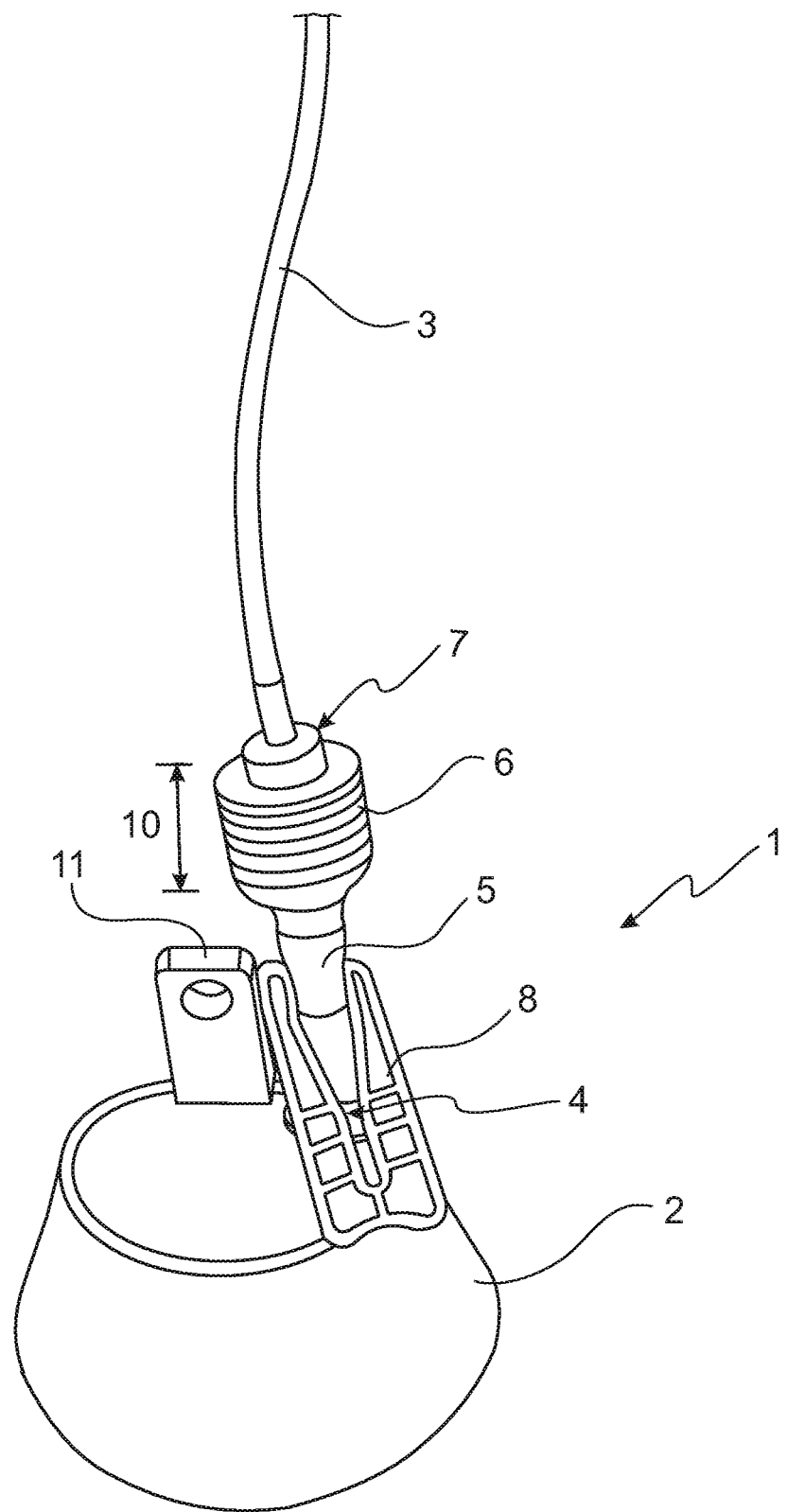
FIG. 1 a schematic view of an embodiment of a system according to the invention with an open inlet opening of the inventive vacuum container.

The system 1 comprises a vacuum container 2 for drainage of fluids or wound secretion, particularly from body and/or tissue openings of the human or animal body. The vacuum container 2 is pre-evacuated, thus it is already provided with the vacuum during manufacturing. Particularly the vacuum container 2 can be pre-evacuated with about 40000 Pascal [Pa] or about 98000 Pascal [Pa]. The pre-evacuation of the vacuum container 2 with about 40000 Pascal [Pa] enables wound drainage according to a so-called low-vacuum drainage and a pre-evacuation of the vacuum container 2 with about 98000 Pascal [Pa] enables wound drainage according to a so-called high-vacuum drainage.

The vacuum container 2 has an inlet opening 4. At the inlet opening 4 of the vacuum container 2 a vacuum indicator 6 is located, precisely a bellow. According to the invention the inlet opening 4 of the vacuum container 2 of the system 1 shown in FIG. 1 is sealable.

The inlet opening 4 of the vacuum container 2 is connected to the vacuum indicator 6 via a tube-like element 5, so that the vacuum indicator 6 is located at the inlet opening 4 of the vacuum container 2. In a preferred embodiment of the invention the vacuum indicator 6 is directly located at the inlet opening 4 of the vacuum container 2.

At the tube-like element 5 presently a slide clamp 8 is mounted. The slide clamp 8 has a recess 12 tapered in a longitudinal direction, wherein the recess 12 at one end of the slide clamp 8 is tapered in such a way, that the tube-like element 5 located inside the recess 12 is clampable or pinched off. The opposing end of recess 12 of the slide clamp 8 on the other hand is wide enough, so that the tube-like element 5 located inside the recess is not clampable or pinched off. If the tube-like element 5 is clamped or pinched of by the slide clamp 8, the inlet opening 4 of the vacuum container 2 is sealed. In the other case, when the tube-like element 5 is not clamped or pinched off by the slide clamp 8, the inlet opening 4 of the vacuum container 2 is open.

From FIG. 1 it can be seen that the vacuum indicator 6 is a bellow. The vacuum indicator 6 is located with an end at the inlet opening 4 of the vacuum container 2. The end opposing the end with the vacuum indicator 6 has a further inlet opening 7, to which presently the drainage line 3 or drainage tube 3 is locatable or as present connected. The drainage of fluids or wound secretion is thus affected via the vacuum indicator 6 into the vacuum container 2. Fluids or wound secretion to be aspirated from a not shown body or tissue opening of the human or animal body are guided through the drainage 3 and through the vacuum indicator 6 into the vacuum container 2. Therefore the vacuum indicator 6 preferably comprises a channel or such the like or builds a channel or such the like, so that the fluids or wound secretion to be aspirated is transportable through the vacuum indicator 6, presently a bellow 6, into the vacuum container 2.

In the embodiment of the system 1 according to FIG. 1 the inlet opening 4 of the vacuum container 2 is open. This is achieved in that the slide clamp 8 located at the tube-like element 5 or the tube part 5 is opened, thus the tube-like element 5 or the tube part 5 is not clamped or pinched off. The vacuum indicator 6 in operating and shows presently a completely contracted bellow as vacuum indicator 6, represented by the double-arrow with numeral 10. The completely contracted bellow 10 indicates that a vacuum is present in the vacuum container 2 because the suction caused by the vacuum contracts the bellow.

Figure 2:
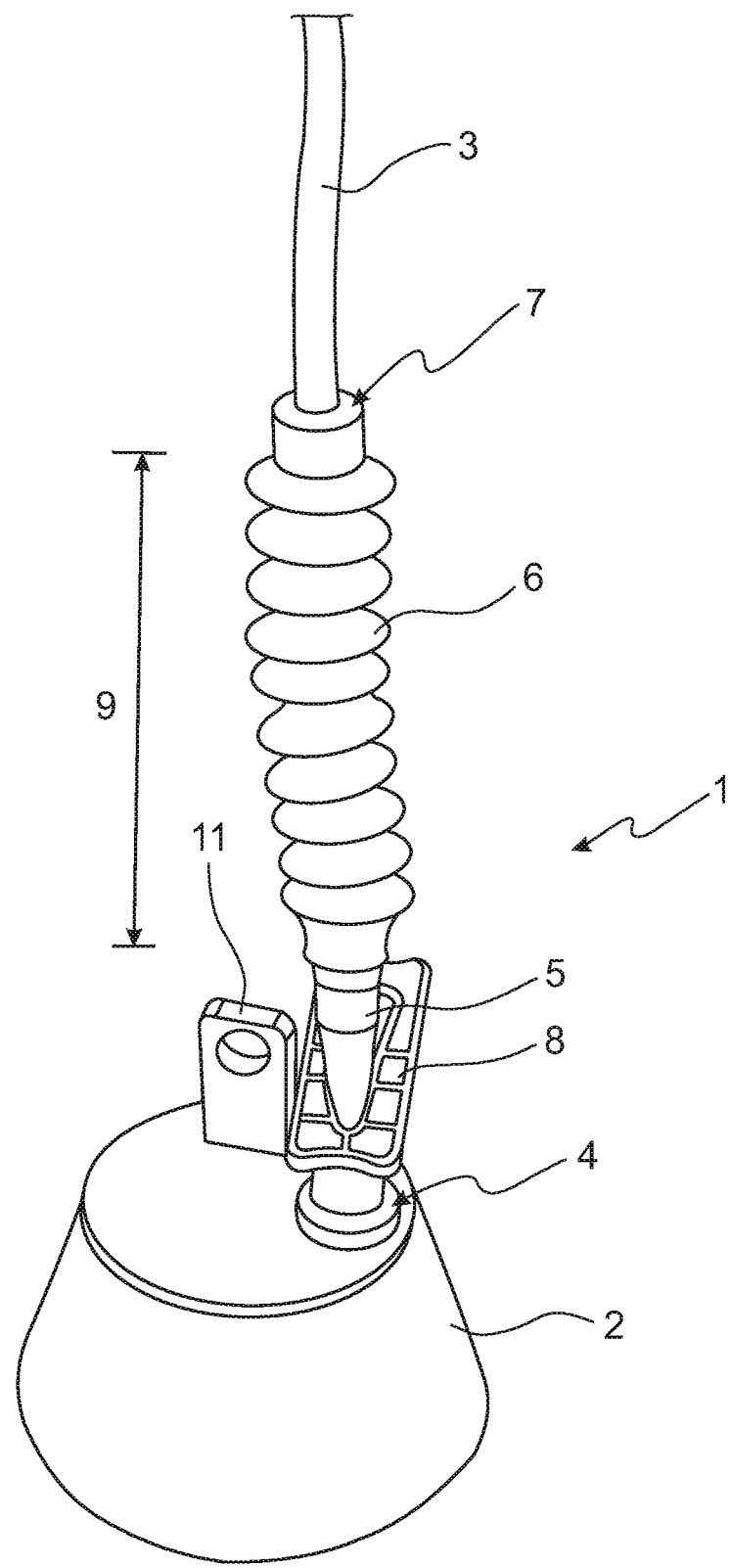
FIG. 2 a schematic view of the embodiment of the inventive system according to FIG. 1 with s closed inlet opening of the inventive vacuum container.

In contrast to this FIG. 2 also shows a vacuum container 2 in which a vacuum is present. However, the slide clamp 8 is in a closed position, so that the inlet opening 4 of the vacuum container 2 is sealed. The bellow as vacuum indicator 6 is completely expanded. This is represented in FIG. 2 by the shown double-arrow with numeral 9. The suction caused by the vacuum inside the vacuum container 2 is not indicated by the vacuum indicator 6 due to the closed inlet opening 4 of the vacuum container 2. For the case that the slide clamp 8 is opened—and thus the inlet opening 4 of the vacuum container 2 is also open—a nevertheless expanded bellow indicates that no vacuum is present inside the vacuum container 2, due to air that has entered the vacuum container 2 and neutralized the former vacuum.

Figure 3:
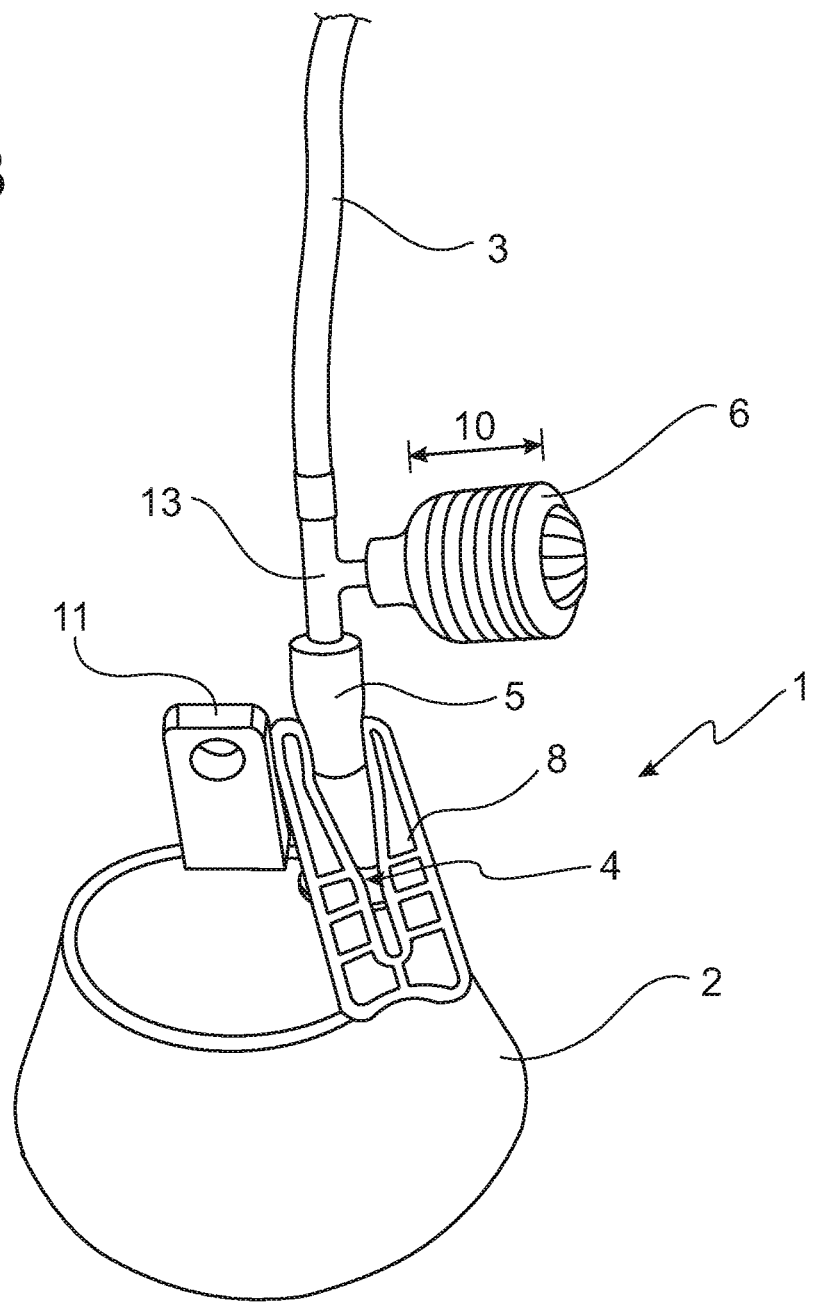
FIG. 3 a schematic view of a further embodiment of an inventive system.

FIG. 3 shows a further embodiment of a system 1 according to the invention, wherein a vacuum indicator 6, presently a bellow, is used, that is closed at one end. The open end of the vacuum indicator 6 is connected to a T-shaped connector 13. The from the viewer seen upper end of the T-shaped connector 13 is presently connected to a drainage line 13 and the lower end of the T-shaped connector 13 is presently connected with a tube-like element 5, wherein the tube-like element 5 is located at the inlet opening 4 of the vacuum container 2. Presently the tube-like element 5 is part of the inlet opening 4 of the vacuum container 2, so that the vacuum indicator 6 is located at the inlet opening 4. The usage of the T-shaped connector 13 allows that the wound secretion or fluid to be aspirated can flow past the vacuum indicator 6.

Presently the tube-like element 5 is clampable or pressable by a slide clamp 8, so that the inlet opening 4 is sealable. Due to the positioning of the T-shaped connector 13 and the vacuum indicator 6 at the inlet opening 4 it is possible that no air enters into the vacuum container 2 by permeation, particularly via the vacuum indicator 6 or the T-shaped connector 13, if the inlet opening 4 is sealed, so that the durability of the vacuum inside of the vacuum container 2, which has been created by a pre-evacuation, is substantially enhanced.

The vacuum container 2 of the system 1 according to the invention shown in FIG. 1 to FIG. 3 has a holder 11 for mounting or hanging to a stand, IV-stand or such a like.

In a further embodiment of the invention the vacuum indicator 6 is integrated into the drainage line 3 or drainage tube 3, so that the vacuum indicator 6 is part of the drainage line 3 or the drainage tube 3.

Advantageously the vacuum container 2 is a so-called Redon-bottle.

The inventive solution enhances the durability of the vacuum of a pre-evacuated vacuum container in that according to the invention the vacuum indicator is provided at the inlet opening and that the inlet opening is sealable. Thus, no air can permeate through the material of the vacuum indicator or through the connection between the vacuum indicator and the vacuum container into the vacuum indicator, particularly after manufacturing and during storage.

The described embodiment shown in the figures is only exemplary and not limiting the invention.

LIST OF NUMERALS

1 System for drainage of fluids or wound secretion
2 vacuum container
3 drainage line
4 inlet opening (vacuum container)
5 tube-like element (tube part)
6 vacuum indicator (bellow)
7 further inlet opening (vacuum indicator)
8 slide-clamp
9 expanded bellow
10 contracted bellow
11 holder 12 recess of slide-clamp
13 T-shaped connector

What is claimed is:

1. A system for drainage of fluid and/or wound secretion, comprising:
    a vacuum container to drain the fluid and/or the wound secretion, wherein the vacuum container is pre-evacuated and includes a sealable inlet opening,
    a vacuum indicator located at the vacuum container inlet opening,
    wherein, during a drainage of fluid and/or wound secretion, the vacuum indicator is arranged such that the drainage of the fluid and/or the wound secretion flows through the vacuum indicator to the vacuum container, and the vacuum indicator is operable to indicate existence of vacuum while the drainage of the fluid and/or the wound secretion flows through the vacuum indicator to the vacuum container,
    wherein the vacuum indicator is connected to the vacuum container inlet opening by a tubular element that is clampable by a clamping device,
    wherein the vacuum indicator comprises a bellow having an inlet end and an outlet end which are separated from one another, and
    wherein, during the drainage of fluid and/or wound secretion, the vacuum indicator is arranged such that the drainage of the fluid and/or the wound secretion flows through the bellow from the inlet end to the outlet end and then to the vacuum container.

2. The system according to claim 1, wherein the inlet end of the bellow is connectable with a drainage line.

3. The system according to claim 2, further comprising the drainage line, and wherein the bellow is disposed between the vacuum container and the drainage line.

4. The system according to claim 1, wherein the vacuum container inlet opening is sealable by the clampable tubular element.

5. The system according to claim 1, wherein the clamping device comprises a slide-clamp.

6. The system according to claim 1, wherein the vacuum container has a capacity in a range of about 100 ml to about 1500 ml.

7. The system according to claim 1, wherein the vacuum container is pre-evacuated in a range of about 40,000 Pascal to about 98,000 Pascal.

8. The system according to claim 1, wherein the bellow is contractable when a vacuum is present inside the vacuum container and the vacuum container inlet opening is open, and expandable when the vacuum is not present inside the vacuum container or the vacuum container inlet opening is closed.

9. A system for drainage of fluid and/or wound secretion, comprising:
    a drainage line, wherein the drainage line has a vacuum indicator, wherein the vacuum indicator is configured to indicate presence of a vacuum,
    wherein, during a drainage of fluid and/or wound secretion, the vacuum indicator is arranged such that the drainage of the fluid and/or the wound secretion flows through the vacuum indicator to a vacuum container, and the vacuum indicator is operable to indicate existence of vacuum while the drainage of the fluid and/or the wound secretion flows through the vacuum indicator to the vacuum container,
    wherein the vacuum indicator is connected to an inlet opening of the vacuum container by a tubular element that is clampable by a clamping device,
    wherein the vacuum indicator comprises a bellow having an inlet end and an outlet end which are separated from one another, and
    wherein, during the drainage of fluid and/or wound secretion, the vacuum indicator is arranged such that the drainage of the fluid and/or the wound secretion flows through the bellow from the inlet end to the outlet end and then to the vacuum container.

10. The system according to claim 9, wherein the vacuum indicator is integrated into the drainage line.

11. The system according to claim 9, wherein the drainage line is configured to connect to the vacuum container.

12. The system according to claim 9, wherein the inlet end of the bellow is connectable with the drainage line.

13. The system according to claim 9, wherein the bellow is disposed between the vacuum container and the drainage line.

14. The system according to claim 9, wherein the vacuum container inlet opening is sealable by the clampable tubular element.

15. The system according to claim 9, wherein the clamping device comprises a slide-clamp.

16. The system according to claim 9, wherein the vacuum container has a capacity in a range of about 100 ml to about 1500 ml.

17. The system according to claim 9, wherein the vacuum container is pre-evacuated in a range of about 40,000 Pascal to about 98,000 Pascal.

18. The system according to claim 9, wherein the bellow is contractable when a vacuum is present inside the vacuum container and the vacuum container inlet opening is open, and expandable when the vacuum is not present inside the vacuum container or the vacuum container inlet opening is closed.

* * * * *